United States Patent [19]
Chalon et al.

[11] 4,232,667
[45] Nov. 11, 1980

[54] SINGLE LIMB BREATHING CIRCUIT ASSEMBLY AND ABSORBER

[76] Inventors: Jack Chalon, 9 Tarry Hill Rd., Tarrytown, N.Y. 10591; Sivam Ramanathan, 7100 Blvd. East, Guttenberg, N.J. 07093; Herman Turndorf, 37 Hyatt Rd., Briar Cliff Manor, N.Y. 10510

[21] Appl. No.: 939,213

[22] Filed: Sep. 5, 1978

Related U.S. Application Data

[63] Continuation of Ser. No. 747,910, Dec. 6, 1976, abandoned, which is a continuation-in-part of Ser. No. 568,279, Apr. 15, 1975, abandoned.

[51] Int. Cl.³ .......................................... A61M 16/00
[52] U.S. Cl. .......................... 128/203.26; 128/203.12; 128/203.28; 128/204.17; 128/205.12; 128/205.17; 128/205.24; 128/911
[58] Field of Search .................. 128/188, 191 R, 194, 128/195, 196, 197, 203, 205, 209, 210, 211, 212, 145.6, 145.8, 142 R, 147; 138/114 R; 55/DIG. 33, DIG. 35, 387, 269; 422/120, 164

[56] References Cited

U.S. PATENT DOCUMENTS

| 1,999,086 | 4/1935 | Claudius | 128/191 R |
|---|---|---|---|
| 2,284,964 | 6/1942 | Mautz et al. | 128/191 R |
| 2,614,561 | 10/1952 | Fox | 128/191 R |
| 2,918,356 | 12/1959 | Hay | 128/191 R X |
| 3,277,890 | 10/1966 | Warncke | 128/202 X |
| 3,507,621 | 4/1970 | Goodman et al. | 128/191 R X |
| 3,707,965 | 1/1973 | Guzay | 128/191 R |
| 3,721,238 | 3/1973 | Wise et al. | 128/188 |
| 3,721,239 | 3/1973 | Myers | 128/188 |
| 3,856,051 | 12/1974 | Bain | 138/114 |
| 4,005,708 | 2/1977 | Netteland et al. | 128/192 R X |
| 4,007,737 | 2/1977 | Paluch | 128/188 |

FOREIGN PATENT DOCUMENTS

| 208565 | 4/1909 | Fed. Rep. of Germany | 128/191 R |
|---|---|---|---|
| 520342 | 7/1920 | France | 128/191 R |
| 51063 | 8/1941 | France | 128/191 R |
| 488666 | 7/1938 | United Kingdom | 128/191 R |

*Primary Examiner*—Henry J. Recla
*Attorney, Agent, or Firm*—Hubbell, Cohen, Stiefel & Gross

[57] ABSTRACT

New and improved single limb breathing circuit assembly for use in a circle absorbed anesthetic system is disposed within and surrounded by the expiratory limb to provide for heating of the inhaled gases by the exhaled gases. Valve means insure that substantially all exhalation occurs in the expiratory limb and that substantially all inhalation occurs in the inspiratory breathing limb to prevent re-breathing of exhaled carbon dioxide. The absorber comprises inlet and internal outlet conduits which combine to assure the flow of gases from the absorber at high humidity levels. Valve means are also provided to proportion the fresh gas inflow to the absorber between the inlet and outlet conduits to enable control of the humidity of the gases flowing from the absorber within a predetermined range. The various portions of the system are arranged so as to minimize both heat and moisture loss in the inhaled gases passing through the absorber for conveyance to the patient.

7 Claims, 6 Drawing Figures

4,232,667

SINGLE LIMB BREATHING CIRCUIT ASSEMBLY AND ABSORBER

This is a continuation, of application Ser. No. 747,910, filed Nov. 6, 1976 and now abandoned, which is a continuation-in-part of our pending application Ser. No. 568,279, filed Apr. 15, 1975 and now abandoned.

BACKGROUND OF THE INVENTION

1. Field of the Invention

This invention relates to a new and improved, single limb breathing circuit assembly for use in circle absorber anesthetic systems, and to a new and improved absorber which is particularly, though not exclusively, adapted for use therewith.

2. Description of the Prior Art

The circle absorber anesthetic systems of the prior art will generally be seen to comprise relatively bulky and heavy double limb breathing circuit assemblies which function to supply relatively cool and dry oxygen and anesthetic mixtures to the patient. Among the more significant disadvantages of these double limb breathing circuit assemblies are the overall unwieldiness and tendency of the same to become entangled and/or simply get in the way during the course of an operation, and/or to become disconnected from the patient. In addition, and particularly in the course of surgery of long duration, the relatively cool and dry gases supplied thereby have a clearly demonstrated physiologically adverse drying effect on the ciliated epithelium of the tracheo-bronchial tree of the patient, and can be conductive to patient hypothermia.

The single limb breathing circuit assemblies of the prior art are generally of the open circuit type which do not separate inhaled and exhaled gases and which suffer from a wide range of significant disadvantages. More specifically, these disadvantages of the single limb breathing circuit assemblies of the prior art include: the necessity for relatively high anesthetic and oxygen inflows to purge carbon dioxide with resultant relatively high anesthetic costs per operation; relatively high levels of re-breathing of carbon dioxide despite all efforts to purge the same with resultant physiologically adverse increase in the secretion of adrenalin by the patient; the supply of relatively dry and cool oxygen and anesthetic mixtures at relatively high flow rates to the patient with resultant physiologically adverse effects on the patient as discussed hereinabove; the anesthetic pollution of the operating room due to the direct venting of the excess anesthetic thereinto with resultant substantial increase in the exposure of operating room personnel to a variety of documented personal risks and, in the case of pregnant female personnel, to the additional risks of spontaneous abortion or serious malformation of the unborn child; the need for special single outlet adaptor means to enable the circuit to function with conventional and very widely used anesthetic supply equipment; the inability of the circuit to provide for patient hyperventilation with resultant lack of utility thereof for use in certain neurosurgical procedures wherein shrinkage of the brain is required and air embolism must be prevented; the inability to provide for spontaneous patient ventilation in the absence of even higher anesthetic and oxygen inflows with resultant even higher levels of anesthetic pollution of the operating room; and the necessity for the use of cumbersome and not always fully reliable nomograms for estimation of anesthetic and oxygen inflows to insure safe ventilation in instances wherein the patient is feverish and/or in a high metabolic state, or a state in which carbon dioxide production by the body is high.

In addition, the absorbers of the prior art will generally be found to be relatively bulky, complex, and expensive and, in many instances, incapable of delivering gases for inspiration by the patient to the breathing circuit at very desirable high temperature and humidity levels. Also, no prior art absorbers are known which include provision for the precise proportioning of the fresh gas inflow from the anesthetic machine between the absorber inlet and outlet to in turn enable precise control in the temperature and humidity of the gases as delivered from the absorber to the inspiratory passage of the breathing circuit for inspiration by the patient.

OBJECTS OF THE INVENTION

It is accordingly, an object of this invention to provide a new and improved, single limb breathing circuit assembly for use in circle absorber systems which is of relatively compact configuration and of relatively light weight, which is resistant to tangling or kinking and which is readily manipulatable during the course of an operation with minimal risk of detachment from the patient.

Another object of the invention is the provision of a breathing circuit assembly as above which is of relatively simple construction and which is easily fabricatable from readily available, inexpensive materials of proven dependability and appropriate physical characteristics.

Another object of the invention is the provision of a breathing circuit assembly as above which provides for substantial increase in the humidity and temperature of the anesthetic and oxygen at the point of delivery to the patient to very significant physiological advantage.

Another object of the invention is the provision of a breathing circuit as above which requires relatively low fresh anesthetic and oxygen inflow rates to thereby reduce the consumption and costs thereof.

Another object of the invention is the provision of a breathing circuit as above which substantially eliminates the rebreathing of carbon dioxide by the patient to very significant physiological advantage.

Another object of the invention is the provision of a breathing circuit as above which eliminates anesthetic pollution of the operating room.

Another object of the invention is the provision of a breathing circuit as above which can readily effect hyperventilation of the patient, and which can effect spontaneous ventilation of the patient at even the lowest of anesthetic and oxygen inflow rates.

A further object of the invention is the provision of a breathing circuit as above which is readily usable with existing anesthetic supply equipment without any modification of the latter.

A still further object of the invention is the provision of a breathing circuit as above which does not require the use of nomograms or special adjustments of the anesthetic supply equipment in the estimation of anesthetic and oxygen inflow rates.

Another object of this invention is the provision of a new and improved absorber which is capable of delivering gases to the inspiratory passage of the breathing circuit at very desirable, high temperature and humidity levels without need for an auxiliary humidifier or analagous source of moisture, and/or external pressure or electrical power sources.

A further object of this invention is the provision of an absorber as above which includes provision for the precise proportioning of the fresh gas inflow from the anesthetic machine between the absorber inlet and outlet conduits to thus enable precise control of the temperature and humidity of the gases delivered from the absorber within a predetermined range.

A further object of the invention is the provision of an absorber as above which is of relatively straightforward construction to thus reduce the cost thereof, and enable the production of the absorber as a disposable item.

A further object of this invention is the provision of an absorber as above which is readily utilizable with the vast majority of anesthetic supply machines in the complete absence of modification of the latter.

A further object of this invention is the provision of an absorber as above which is particularly, though not exclusively, adapted for use with the breathing circuit of the invention.

A further object of the invention is the provision of an absorber as above which functions to sterilize the expired gases to thus prevent contamination of the ventilator and/or rebreathing bag.

SUMMARY OF THE INVENTION

The new and improved single limb breathing circuit assembly of the invention is for use in a circle absorber anesthetic system and comprises an inspiratory breathing limb which is disposed within and surrounded by the expiratory limb to thus provide for a substantially less cumbersome assembly and for the advantageous heating of the inhaled gases by the exhaled gases with resultant increase on the part of the former to hold moisture and attendant decrease in the drying and cooling effects of the inhaled gases on the anesthetized patient. Valve means restrict patient inhalation to the inspiratory breathing passage and patient exhalation to the expiratory passage to thus prevent re-breathing of exhaled carbon dioxide by the patient to further advantage. In addition, since the system can be closed, anesthetic pollution of the ambient operating room air can be prevented.

The new and improved absorber of the invention comprises an outlet conduit which extends from the hot and highly humid space at the bottom of the absorber through the absorber lime charge, and an inlet conduit which delivers the expired gases from the breathing circuit to the space atop the absorber lime charge. As a result, the expired gases which are delivered to the absorber inlet from the expiratory passage of the breathing circuit, are forced to pass through the reacting lime charge and said hot and humid space, and are maintained at relatively high temperature levels during the passage thereof through said outlet conduit to insure the delivery thereof from the absorber at high humidity levels. The passage of the expired gases through the reacting lime charge is additionally effective to sterilize the same and prevent contamination of the ventilator and/or breathing bag. Proportioning valve means are provided to enable precise proportioning of the relatively cool and dry fresh gas inflow from the anesthetic machine between the inlet and outlet conduits of the absorber to thus enable precise control in the humidity of the gases delivered from the absorber within a predetermined range. In addition, the absorber inlet conduit is arranged to surround and heat the absorber outlet conduit to maintain the gases exiting from the absorber at relatively high temperature and humidity levels prior to the delivery thereof to the inspiratory passage of the breathing circuit. The absorber is readily utilizable with the vast majority of anesthetic supply machines without any modification of the latter.

DESCRIPTION OF THE DRAWINGS

The above and other objects and advantages of the invention are believed made clear by the following detailed description thereof taken in conjunction with the accompanying drawings wherein.

DETAILED DESCRIPTION OF THE INVENTION

Figure 1:
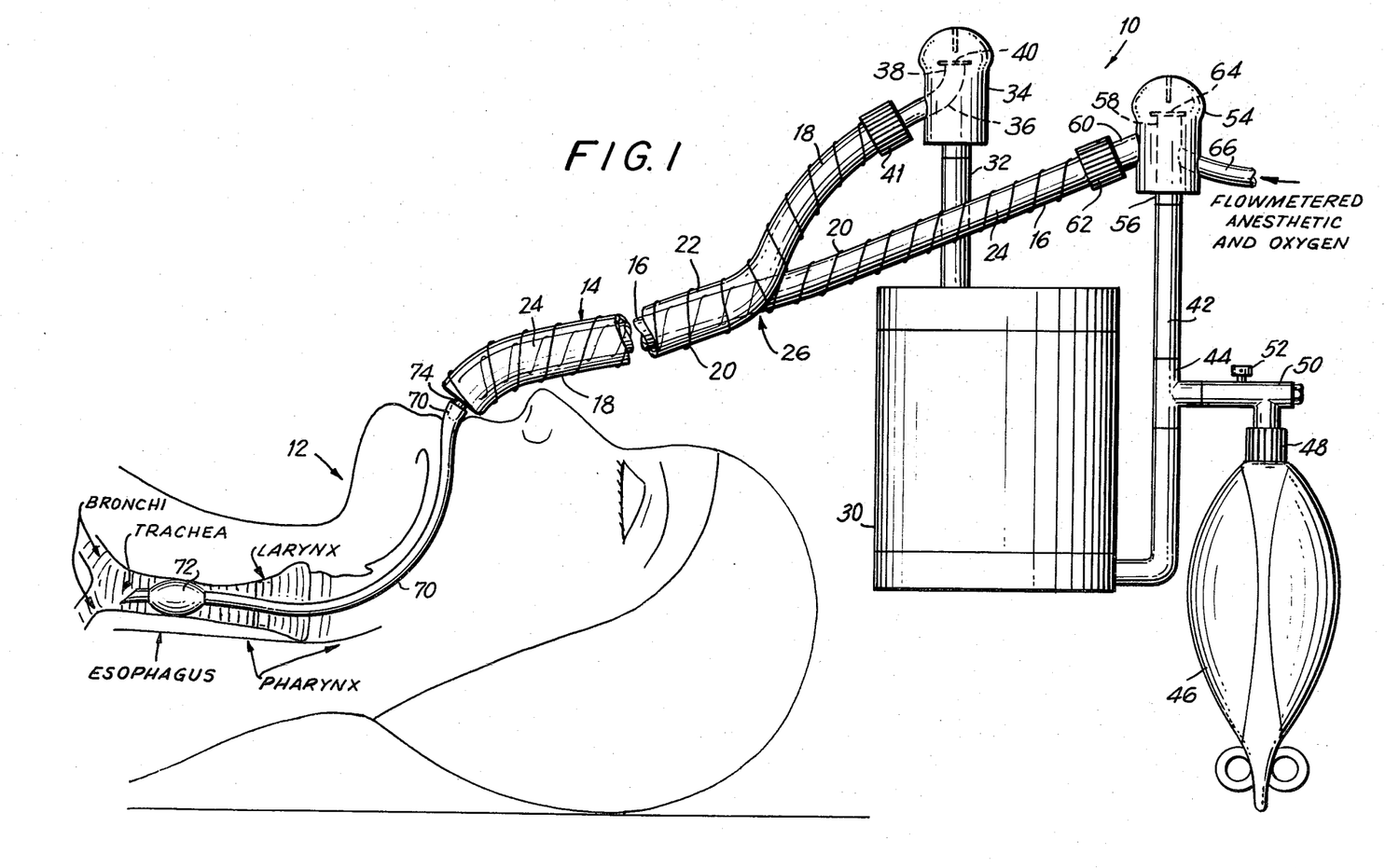
FIG. 1 is a side elevational view of the breathing circuit of the invention in operable combination with a prior art absorber, with parts cut away and parts in cross section for purposes of clarity of illustration.

Referring now to FIG. 1, a circle absorber anesthetic system is indicated generally at 10. The anesthetic system 10 comprises a new and improved single limb breathing circuit assembly 14 which is constructed and operative in accordance with the teachings of our invention. For purposes of clear illustration of function, the anesthetic system 10 is depicted in operative relationship with the head and neck of a patient 12; it being of course the function of the anesthetic system 10 to anesthetize the patient 12 in the improved manner described in detail hereinbelow through use of the single limb assembly 14.

The single limb breathing circuit assembly 14 includes a tubular inspiratory limb 16 and a tubular expiratory limb 18. Each of the inspiratory limb 16 and the expiratory limb 18 are preferably constructed from a suitably conductive and flexible, readily available plastic material in the nature, for example, of extruded PVC which is, of course, readily and economically disposable. Spaced reinforcing ribs 20 are provided as shown on each of the limbs, and function to strengthen the same and inhibit kinking thereof. Preferably, at least the expiratory limb 18 is generally transparent to allow observation of the interior thereof, although this is not of critical importance.

Throughout substantially the entire longitudinal extent of the single limb breathing circuit assembly 14, the inspiratory limb 16 may be seen to be of substantially lesser diameter than the expiratory limb 18 and to be disposed within the latter in generally concentric relationship thereto. This results in the formation by the space between the interior wall of the expiratory limb 18 and the exterior wall of the inspiratory limb 16 of a generally donut-shaped expiratory passage 22, and the formation by the interior of the inspiratory limb 16 of a generally circular inspiratory passage 24 which is generally concentric with said expiratory passage and is surrounded thereby. Although not shown, it may be understood that suitably apertured spacer rings or spacer ribs or the like may be interposed within the expiratory limb 18 to contact and maintain the inspiratory limb 16 in generally concentric relationship thereto if considered necessary. The respective diameters of the inspiratory limb 16 and the expiratory limb 18 are chosen to provide for inspiratory and expiratory passage cross-sectional areas which are each at least as large, or larger, than the cross-sectional area of the trachea of patient 12 to thus insure that no untoward resistance is provided thereby to the breathing of the patient. This is of particular importance regarding the single limb breathing circuit assembly 14 of our invention since, unlike the single limb assemblies of the prior art, the inspiratory passage 24 of assembly 14 is the breathing passage for patient inspiration. In addition, the ratio between the respective diameters of the inspiratory limb 16 and the expiratory limb 18 is preferably predetermined to provide for substantial equality of inspiratory and expiratory passage cross-sectional areas throughout the longitudinal extent of the single limb assembly 14.

The respective expiratory and inspiratory limbs 18 and 16 are schematically depicted as branching from the single limb assembly 14 by the simple extension of the latter through the wall of the former in air-tight manner as indicated at 26. Alternatively, a fluidic T-piece of common and well known construction may be utilized for this purpose.

A cannister absorber for the absorption of carbon dioxide is indicated at 30 and may, for example, utilize barium hydroxide lime, U.S.P., as the carbon dioxide absorbant. An inlet conduit 32 extends upwardly from the top of the absorber 30, and an expiratory valve which may, for example, take the form of the somewhat schematically depicted dome valve 34, is connected as shown to said inlet conduit. The dome valve 34 comprises a valve inlet conduit 36 which terminates in a valve seat 38, and a valve member 40 is disposed as shown on said valve seat in such manner as to permit fluid flow through the valve only in the direction of the absorber 30 as should be obvious.

A quick disconnect fitting is indicated at 41 and functions as shown to connect the outlet end of the expiratory limb 18 to the valve 34 to thereby provide for fluid flow from said expiratory limb through the valve and into the absorber 30.

An outlet conduit 42 extends as shown upwardly from the bottom of the absorber 30, and a T-fitting 44 is connected in said outlet conduit. An anesthesia bag which may, for example, be of 3-5 liter capacity, is indicated at 46 and is connected as shown through quick disconnect fitting 48 and fitting 50 to the outlet conduit 42 of the absorber to thus provide for fluid flow between the bag and said outlet conduit, and vice versa. A pressure relief valve is indicated at 52 and is set to vent the system to atmosphere in the event that system pressure exceeds a safe level as may, for example, occur periodically during the use of high fresh gas inflow rates. As an alternative to anesthesia bag 46, it will readily be understood by those skilled in this art that suitable ventilator means may be connected to absorber outlet conduit 42 through quick disconnect fitting 48 for use, for example, in those cases wherein the patient were paralyzed by muscle relaxants introduced to produce muscle relaxation for surgical purposes.

An inspiratory valve which may again, for example, take the form of the somewhat schematically depicted dome valve, is indicated at 54 and is connected as shown at the end of absorber outlet conduit 42. The valve 54 comprises a valve inlet conduit 56 which terminates in a valve seat 58, and a valve outlet conduit 60 which is connected as shown through quick disconnect fitting 62 to the inlet end of inspiratory limb 16. A valve member 64 seats as shown on valve seat 58 in such manner as to permit fluid flow through inspiratory valve 54 from absorber outlet conduit 42 into inspiratory limb 16.

A gas inlet conduit is shown at 66 and functions as indicated to provide fresh anesthetic and oxygen to the system 10 from non-illustrated, flow-metered sources thereof by introducing the same into valve inlet conduit 56 in the manner depicted.

An endotracheal tube is indicated at 70 and is operatively positioned as shown in the throat of the patient 12 to terminate in the patient's trachea short of the bronchi. A cuff 72 is provided adjacent the inner end of the endotracheal tube 70 to form a substantially fluid-tight seal with the wall of the trachea and thus insure that all gases inhaled and exhaled by the patient travel through said tube. The patient end of the expiratory limb 18 terminates as shown in a necked down, tubular portion 74 which is complimentarily sized and shaped relative to the adjacent end of the endotracheal tube 70, and the latter is inserted in the portion 74 in any appropriately tight-fitting and fluid-tight manner to thus provide for unobstructed fluid flow between the interior of the endotracheal tube and each of the expiratory passage 22 and the inspiratory passage 24 of the single limb assembly 14.

By the above description is believed made clear that a substantially closed fluid flow circuit is provided to extend from the trachea of the patient 12, through the endotracheal tube 70, expiratory passage 22, expiratory limb 18, expiratory valve 34, carbon dioxide absorber 30, inspiratory valve 54, inspiratory limb 16, inspiratory passage 24 and the endotracheal tube 70, respectively, back to the patient's trachea; with the fresh gas inlet conduit 66 and the anesthesia bag 46 each being in free fluid flow communication with said circuit.

In use, for example, with the anesthestic halothane during the conduct of typical surgery requiring the opening of the abdomen, chest or skull to thus dictate the use of endotracheal tube 70, and assuming steady state or equilibrium patient and anesthesia system conditions to have been reached as should be the case after the first 60–90 minutes of the operation, it may be understood that the patient will be breathing spontaneously or mechanically approximately 12–14 times per minute to thus require a total flow fresh gas inflow through supply conduit 66 of from 500 to 5000 cc per minute. Of this total flow, from 495 to 4800 cc per minute will be oxygen for obvious purpose, while the remaining 5 to 200 cc per minute will be halothane vapor to maintain the required level of patient anesthesia.

Under these conditions and commencing the description of the operation of the anesthetic system 10 upon exhalation by the anesthetized patient, the gases exhaled by the patient from endotracheal tube 70 into the single limb assembly 14 will be at approximately the body temperature of patient 12, or between 32° C. and 34° C., will be substantially saturated or at 99% relative humidity to contain approximately 35-38 mg/L of water vapor, will of course be of reduced oxygen content, will contain additional carbon dioxide for a total of approximately 5% by volume of carbon dioxide, and will contain a not insubstantial part (perhaps as high as 1.0% by volume) of the halothane anesthetic which was introduced to the patient through inspiratory passage 24 as described in detail hereinbelow. Of course, the exhalation of the highly humid or saturated gases will have a marked cooling effect on the body of the patient 12 as a result of the loss of the heat of vaporization which must be provided by the body to vaporize the exhaled water. Unless counteracted, this heat loss, in conjunction with an ambient operating room temperature of 22° C., or 15° C. lower than the patient's body temperature, and probable exposure of large areas of the patient's body to this ambient temperature, can result in accidental hypothermia with attendant post-operative shivering and increased use of oxygen by the patient at a time when the same is most needed for maintenance of essential body functions.

As the exhaled gases enter the single limb assembly 14, the same will flow through the expiratory passage 22 and the expiratory limb 18 to the expiratory valve 34, it being believed clear that flow of the exhaled gas through the inspiratory passage 24 will be prevented by the ambient passage pressure as maintained by the one-way action of the inspiratory valve 54. Flow of the exhaled gases through the expiratory passage 22 will, of course, function to heat the gases in the inspiratory passage 24, which is surrounded thereby, and this is of very significant advantage as described in detail hereinbelow. Too, the gradual cooling of the exhaled gases by heat exchange with the inspired gases, and with the cooler ambient operating room air, which surrounds the expiratory limb 18, will result in the condensation of some of the water vapor from the exhaled gases and the collection thereof as moisture on the inner and outer walls of the expiratory passage 22, and within the expiratory limb 18 beyond the single limb assembly 14. With the patient 12 disposed on his back in the manner depicted in FIG. 1, it may readily be understood that some of this condensed moisture wall, of course, find its way under the force of gravity to the interior of the endotracheal tube 70 for advantageous pick-up by the inspired gases as explained in greater detail hereinbelow.

The exhaled gases will flow through expiratory valve 34 and into absorber 30 through absorber inlet conduit 32 for substantial absorption of the carbon dioxide included in said gases. This absorption is accomplished by exothermic reaction with the barium hydroxide lime active ingredient of the absorber 30 with attendant production of water and liberation of heat to thus result in the addition of substantial water vapor to the exhaled gases and concomitant increase in the temperature thereof to enable the gases to maintain a greater percentage of water vapor therein as should be obvious. As a general observation, it may be understood that the exhaled gases will exit the absorber at a temperature of approximately 46° C. and a relative humidity of approximately 99%.

As the now substantially carbon dioxide-free exhaled gases leave the absorber, the same flow upwardly through absorber outlet conduit 42 to thus place the same in free fluid flow communication with the anesthesia bag 46, with the primary function of the latter being to act as a fluid reservoir to fill in the difference between the gases supplied by the remainder of the anesthetic system 10 to the patient and the actual needs of the patient. In addition, and in the event of indication of cessation of breathing by the patient, compression of the bag will, of course, function in the manner of a ventilator to maintain breathing.

Flow of the exhaled gases through absorber outlet conduit 42, and the exposure of the latter to the ambient temperature of the operating room, will result in the temperature of the exhaled gases approximating said ambient temperature with resultant condensation of some water vapor and collection thereof in the lower portions of the absorber 30 and the anesthesia bag 46.

Assuming at this juncture in the description of the anesthetic system 10 that inhalation is now commenced by the patient 12, it may be understood that this results in the flow of what now will be termed the inhaled gases into and through inspiratory valve 54 with attendant admixture of the inhaled gases and the fresh, and very dry, halothane anesthetic and oxygen which are introduced into the inspiratory valve through supply conduit 66, and flow of the resultant mixture of residual or exhaled gases from the absorber 30 and/or the anesthesia bag 46, and the freshly supplied halothane anesthetic and oxygen, through inspiratory valve 54 into the inspiratory limb 16. As this inhalation commences, it may be understood that the closure of the expiratory valve 34, which occurred at the termination of exhalation, will substantially prevent the re-breathing of any of the exhaled gases which then occupy the expiratory passage 22 to thus substantially prevent the re-breathing of carbon dioxide to very significant advantage as discussed in greater detail hereinbelow. This closure of the expiratory valve 34 of necessity insures that substantially all of the gases inhaled by the patient 12 (with the obvious exception of those disposed in the endotracheal tube 70) during inhalation will be supplied through inspiratory passage 24 in limb 16 to thus make clear that the latter does in fact function as the inspiratory breathing limb in the circuit assembly of the invention. This differs markedly from the single limb circuit assemblies of the prior art wherein the fresh anesthetic and oxygen supplied through the fresh gas delivery limb and delivered to, and mixed with the exhaled gases, in the expiratory passage to "slosh" back and forth therewith in the latter; and wherein the gases inhaled by the patient are supplied substantially by the resultant fresh gases-exhaled gases mixture from the expiratory passage with only a relatively small portion thereof being constituted by the fresh anesthetic and oxygen. This of necessity, results in the re-breathing of some carbon dioxide—at a rate determined by the fresh gas inflow rate and whether the patient is breathing spontaneously or mechanically—and, in any event, makes clear that the fresh gas inflow limb of the prior art single limb breathing circuit does not function as the breathing limb.

Flow of the inhaled gases from inspiratory limb 16 into and through the inspiratory passage 24 follows, with the higher temperature exhaled gases in the surrounding expiratory passage 22 functioning to heat the inhaled gases throughout substantially the entire extent of the single limb assembly. As a result, the inhaled gases will reach the juncture of the single limb assembly 14 and the endotracheal tube 70 at a substantially higher temperature than would prevail in the case of the double limb systems of the prior art, and this is of very significant advantage with regard to both the prevention of patient hypothermia as discussed hereinabove, and the increase in the ability of the exhaled gases to pick-up and hold moisture.

More specifically, it may be understood that carefully controlled and monitored tests at stabilization of the single limb breathing circuit assembly 14 of the invention, and of a conventional two limbed closed circuit assembly of the prior art, at the same representative levels of expired minute volume of carbon dioxide, have established an inhaled gases temperature at the juncture with the endotracheal tube of from 28.1° C. to 28.56° C. for the former as opposed to an inhaled gases temperature at this same juncture of from only 23° C. to 24° C. for the latter. With the inhaled gases in each instance at 60% relative humidity, this temperature difference transcribes into an ability on the part of the inhaled gases as provided by the single limb breathing circuit assembly 14 of the invention to hold from 15.38 mg/L to 16.47 mg/L of water as opposed to from only 12.3 mg/L to 12.6 mg/L of water for the inhaled gases of the prior art circuit assembly under discussion, all as clearly set forth directly hereinbelow in Table A.

TABLE A

| Type of Circuit | Minute Volume of Expired $CO_2$ (ml) | Inspired Gas Temperature °C. | Inspired Relative Humidity % | Inspired Absolute Humidity mg/L |
|---|---|---|---|---|
| Prior Art Closed Two Limb Closed | 150 | 23° C. | 60% | 12.3 |
| | 200 | 24° C. | 60% | 12.6 |
| Single Limb of Invention | 150 | 28.1° C. | 60% | 16.38 |
| | 200 | 28.56° C. | 60% | 16.47 |

As a result of this significantly increased ability of the inhaled gases of the breathing circuit assembly of the invention to hold moisture rather than to allow the same to condense out as would be the situation in a double limb circuit assembly of the prior art wherein the inspiratory limb would be exposed to the relatively low ambient temperature of the operating room, the inhaled gases will arrive at the juncture of the single limb assembly 14 and endotracheal tube 70 with greater moisture content than will those of the double limb prior art circuit assembly. In addition, the increased ability of the warmer inhaled gases to pick-up moisture, and the presence of moisture in the portion 74 of the expiratory limb 18 and the endotracheal tube 70 under circumstances wherein the patient 12 is disposed on his back, will in fact result in the pick-up and holding of some of said moisture by the inhaled gases as the same traverse the endotracheal tube and, in this regard, the breathing circuit assembly 14 of the invention may be understood to function in the manner of what might be termed an "improved artificial nose."

The overall result of all the above, will, of course, be the most advantageous delivery of inhaled gases of substantially increased moisture content to the patient 12 with resultant significant inhibition of the drying effect of the inhaled anesthetic gases upon the ciliated epithelium of the tracheobronchial tree. A particularly comprehensive treatment of the physiologically adverse effects of such drying, and attendant cellular damage, is found in the article "Effects of Dry Anesthetic Gases on Tracheobronchial Ciliated Epithelium" by Jack Chalon, M.D., et al., as published in Vol. 37, No. 3 of "ANESTHESIOLOGY" on Sept. 3, 1973.

Since the patient end of the inspiratory limb 16 is disposed in close proximity to the patient end of the expiratory limb 18, as clearly illustrated in the drawing, it may be understood that a minimum of dead space, in which the carbon dioxide-laden exhaled gases can collect for direct rebreathing by the patient, is assured. Thus, and although actual test data is not complete, it now appears that patient re-breathing of carbon dioxide is substantially eliminated (or at least reduced to levels which are almost impossible to detect) through use of the single limb breathing circuit assembly 14 of the invention; and this may readily and advantageously be contrasted with the single limb breathing circuit assemblies of the prior art wherein levels of carbon dioxide re-breathing of as high as 3.0% by volume of the inhaled gases are believed to occur. The disadvantages of re-breathing of relatively high levels of carbon dioxide are well known to include increased adrenalin secretion with attendant respiratory rate increase, changes in the acidity of the blood, and possible cardiac arrythmia or arrest.

Regarding the reduced oxygen and anesthetic requirements made possible by the breathing circuit assembly 14 of the invention when compared to those of the single limb circuit assemblies of the prior art, it may be understood that the closed circuit nature of the circuit assembly 14 taken in conjunction with the fact that the respective approximately 1.0% by volume at partial pressure of the halothane anesthetic, and reduced but still present oxygen, contents of the exhaled gases are recirculated as described, function to substantially reduce oxygen and anesthetic needs for maintenance of steady state of equilibrium patient and anesthetic system conditions. More specifically, actual tests have now established that a reduction of as much as 80% in system oxygen and anesthetic requirements can be achieved. Thus, for example, for a single operation of four hour duration with an anesthetic cost averaging $3.50 per hour, to total $14.00, it may be seen that as much as $11.20 may be saved through use of the system of the invention.

Regarding anesthetic pollution of the operating room which is a major problem with the single limb circuit assemblies of the prior art wherein the expiratory passage is in direct fluid flow communication with the ambient air of the operating room and abnormally high anesthetic inflow rates are required to purge carbon dioxide from the expiratory passage, it is believed clear that this problem is substantially eliminated by the single limb breathing circuit assembly 14 of the invention. Thus the exposure of operating room personnel to the risks of lymphoma, spontaneous abortion, and/or fetal anomalies or fetal malformations are likewise substantially eliminated.

The significant physical advantages of the single limb breathing circuit assembly 14 as opposed to the double limb breathing circuit assemblies of the type particularly prevalent in the prior art may readily be understood to include a less cumbersome and more easily manipulatable circuit assembly, one which is much less likely to detach itself from the patient, substantial reduction in inhibition by the circuit assembly of access to the patient, and substantial elimination of the problem of limb twisting or entanglement with resultant kinking and interruption of gas flow.

Although described by way of example in conjunction with the use of the anesthetic halothane, it is believed clear that the breathing circuit assembly 14 of the invention is by no means limited thereto, but rather, is useful with any one of a very wide variety of known and acceptable anesthetics. Too, although described in conjunction with specific flow rates, percentages, temperatures and/or relative humidity levels or the like, it is believed clear that these are specified for purposes of example, only, and that the same may vary quite widely under different operation conditions and with different patients. Also, although described in conjunction with use of an endotracheal tube, it is to be understood that the breathing circuit assembly of the invention is equally useful with a conventional anesthesia mask.

Although not shown, it should be obvious to those skilled in this art that suitable means would be employed to prevent breathing by the patient 12 through the nose in the event of use of the endotracheal tube 70.

Additional, and particularly carefully monitored testing of the breathing circuit assembly 14 has revealed that the excess moisture in the warm and humid gases emerging from the absorber 30 tend to rain out as those gases reach the inspiratory dome valve 54. This results in water droplets condensing on the surface of the valve member 64 and the latter acting in the manner of a built-in nebulizer during inspiration by the patient to re-introduce this moisture into the inspired gases. In addition, water droplets are deposited on the inner surface of the inspiratory limb 24 during the passage of the inspired gases therethrough, and these water droplets are re-vaporized into the inspired gases by the heating of limb 24 by the expired gases during patient exhalation. It is the combination of these factors which are now believed to be mainly responsible for the advantageous elevation of humidity in the inspired gases, all as set forth in greater detail in the article "A Compact, Well-humidified Breathing Circuit for the Circle System" by Sivam Ramanathan, M.D., Jack Chalon, M.D. and Herman Turndorf, M.D. as published at pages 238–242 of ANESTHESIOLOGY, Vol. 44, No. 3, of March, 1976.

Figure 2:
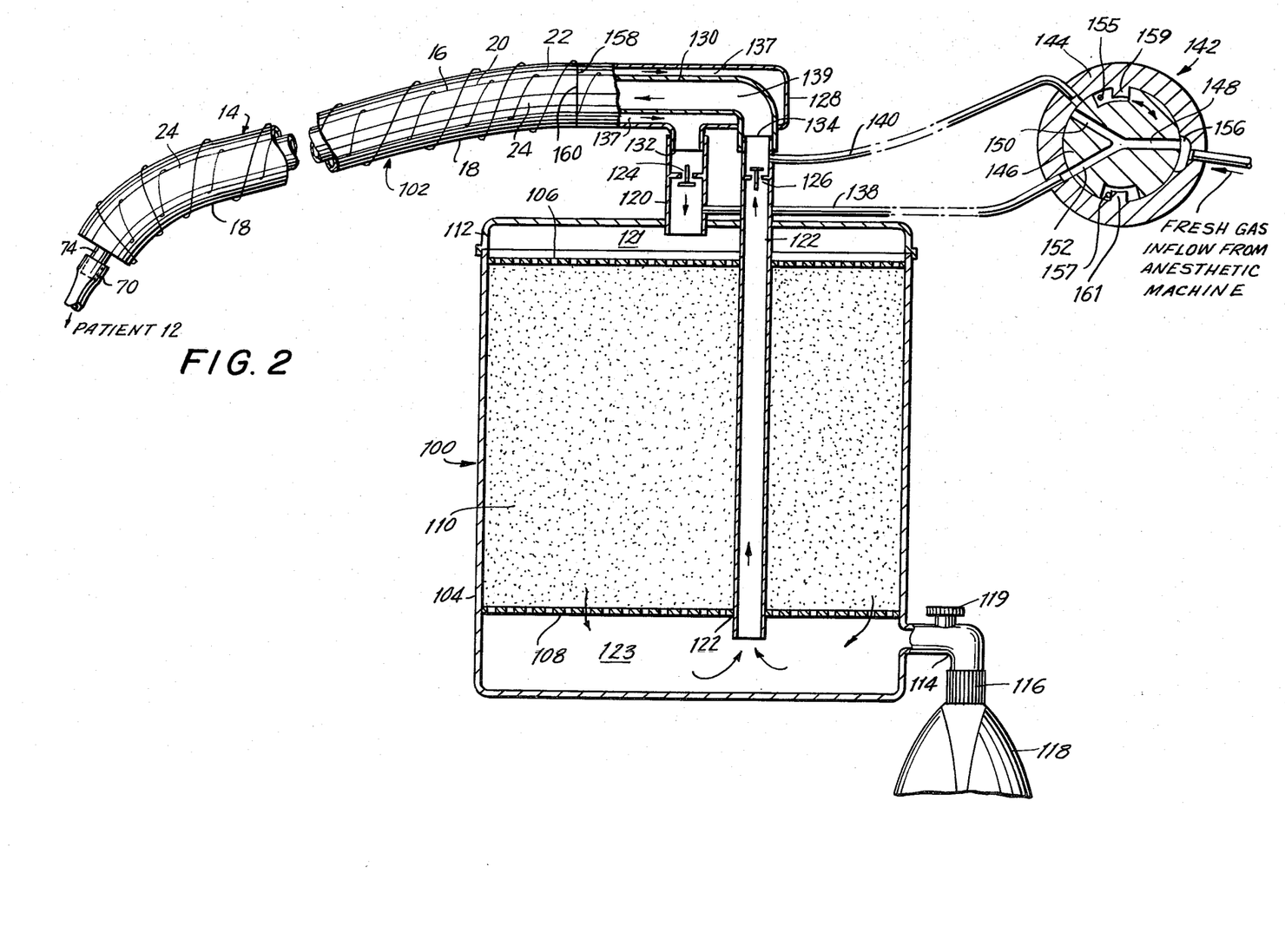
FIG. 2 is a side elevational view of the absorber of the invention in operable combination with the breathing circuit of the invention, and again includes parts broken away and parts in cross-section.

Referring now to FIG. 2, a new and improved absorber constructed and operative in accordance with the teachings of our invention is indicated generally at 100, and is depicted in novel combination with a new and improved, single limb breathing circuit of our invention as indicated generally at 102. The absorber 100 comprises a generally cylindrical cannister 104 having spaced, generally circular mesh-like support members 106 and 108 extending thereacross as shown. A charge of an appropriate carbon dioxide absorbant, for example barium hydroxide lime U.S.P., is indicated at 110 and is contained and supported within cannister 104 by mesh-like support members 106 and 108. A cover 112 is provided for cannister 104 and is readily detachable therefrom to enable replenishment of the barium hydroxide lime 110 upon removal of mesh-like support member 106. Alternatively, a filling port may be provided.

A conduit 114 extends as shown from the lower portion of cannister 104 and connects as indicated through quick disconnect fitting 116 to rebreathing bag 118. Alternatively, non-illustrated ventilator means may, of course, be connected to conduit 114 through fitting 116. A pressure relief valve is indicated at 119 and functions in the manner described hereinabove with regard to valve 52 of FIG. 1.

A tubular inlet conduit is indicated at 120 and extends as shown through cover 112 into fluid flow communication with the space 121 at the top of absorber cannister 104. A tubular outlet conduit is indicated at 122 and extends as shown from fluid flow communication with the space 123 at the bottom of the absorber cannister 104 through the barium hydroxide lime 110 and cannister cover 112 to without the cannister 104. Preferably, the respective cross-sectional areas of the inlet conduit 120 and the outlet conduit 122 are made substantially equal.

A one-way check valve is schematically depicted at 124 and is disposed as shown within inlet conduit 120 so as to permit fluid flow therethrough only into the cannister 104 in the direction indicated by the arrow.

A one-way check valve is schematically depicted at 126 and is disposed as shown within outlet conduit 122 so as to permit fluid flow therethrough only from the cannister 104, again in the direction indicated by the arrow.

The inlet conduit 120 extends as shown from cannister 104 into a generally T-shaped configuration to include an enlarged, tubular inlet conduit portion 128; while the outlet conduit 122 extends as shown into a generally L-shaped configuration to include a tubular outlet conduit portion 130 which projects in fluid-tight manner through a suitable aperture formed therefor in enlarged inlet conduit portion 128 and extends through the latter to be substantially surrounded thereby and generally coextensive thereof. If required by manufacturing considerations, the respective inlet and outlet conduits, and conduit portions may, of course, be made as separate pieces and joined together in any suitably fluid-tight and readily detachable manner, as for example by telescopic connections, at appropriate locations, all as indicated simply by lines 132 and 134 in FIG. 2.

Preferably, the cross-sectional area of the enlarged inlet conduit portion 128 is chosen so that the cross-sectional area of the torus-like flow passage 137 formed between the same and the exterior of outlet conduit portion 130 will be substantially equal to the cross-sectional area of the flow passage 139 formed in said outlet conduit portion; it being understood that the respective cross-sectional areas of the inlet and outlet conduits 120 and 122 are preferably also made equal to each other and to the cross-sectional areas of said passages.

Supply conduits for the supply of fresh anesthetic and oxygen are indicated at 138 and 140 and are respectively connected as shown to inlet conduit 120 and outlet conduit 122 to supply anesthetic and oxygen thereto. Again, these connections may be effected in any suitable fluid tight and readily detachable manner.

A proportioning valve is somewhat schematically depicted at 142 and comprises a housing 144 within which is rotatably disposed a valve member 146. Each of supply conduits 138 and 140 extends as shown through valve housing 144 into communication with the surface of the valve member 146. A generally Y-shaped flow passage comprising connected branches 148, 150 and 152, extends as shown through valve member 146; while a main anesthetic and oxygen supply conduit 154 extends as indicated from a non-illustrated, suitably flow-metered source of the same through valve housing 144 into communication with an arcuate groove 156 formed in said valve housing. With valve member 146 positioned as depicted in FIG. 2, it will be clear that all of the anesthetic and oxygen from main supply conduit 154 will be directed by valve 142 into cannister inlet conduit 120 through valve groove 156, valve passage branches 148 and 152, and supply conduit 138, respectively. Conversely, with valve member 146 rotated to the position depicted in FIG. 2A, it will be clear that all of the oxygen and anesthetic from main supply conduit 154 will be directed by valve 142 into cannister outlet conduit 122 through valve groove 154, valve passage branches 148 and 150, and supply conduit 140, respectively. Alternatively, and with valve member 146 rotated to any position thereof between the valve member positions of FIGS. 2 and 2A, it will immediately become clear to those skilled in this art that some of the anesthetic and oxygen from main supply conduit 154 will be supplied to cannister inlet conduit 120 through supply conduit 138, while the remainder of said anesthetic and oxygen will be supplied to cannister outlet conduit 122 through supply conduit 140. Thus, and after precise calibration of proportioning valve 142 has been effected by actual test measurements, it may be understood that precise proportioning of the respective supplies of anesthetic and oxygen to cannister inlet conduit 138 and cannister outlet conduit 140 will be readily accomplishable.

Figure 2A:
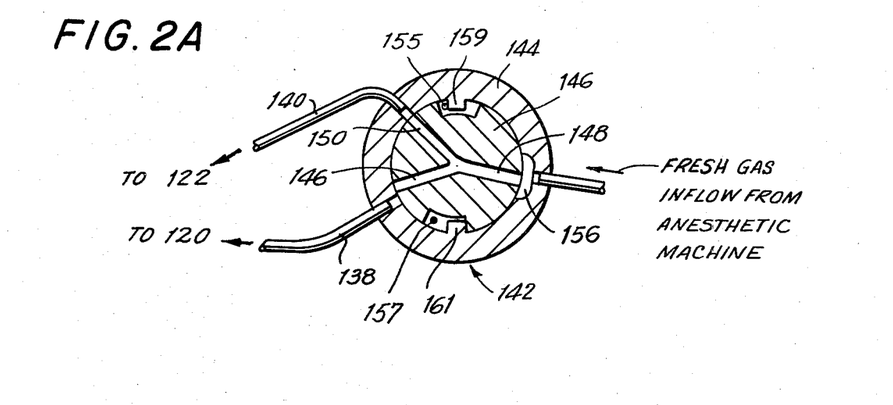
FIG. 2A is a somewhat schematic, cross-sectional view of the proportioning valve of the absorber of FIG. 2 in a different operational position thereof.

Stop means as illustrated schematically in FIGS. 2 and 2A at 155 and 157 on valve member 146, and at 159 and 161 on valve housing 144, are respectively provided to cooperate as shown to positively restrict the rotation of the valve member 146 to the range between the positions of FIGS. 2A and 2B and thus render impossible any inadvertent cut-off of the fresh gas inflow to the absorber 100 by proportioning valve 142.

For use of the single limb breathing circuit of FIG. 1 with the absorber 100 of FIG. 2, it will be clear that the extension of the inspiratory limb 16 through the expiratory limb 18 (as indicated at 26 in FIG. 1), and the resultant branched portions of said inspiratory and expiratory limbs, are eliminated; and the respective, generally concentrically disposed expiratory and inspiratory limbs 18 and 16 connected as simply indicated in FIG. 2 by lines 158 and 160, again in any suitably fluid-tight and readily detachable manner, to the respective portions 128 and 130 of the cannister outlet and inlet conduits 128 and 130. Of course, the respective diameters of the tubular inlet and outlet conduit portions 128 and 130 are made substantially equal to those of the expiratory and inspiratory limbs 18 and 16, although suitable and operationally inconsequential allowances would be made in those diameters if, for example, telescopic connections were to be used at 158 and 160. As an alternative to the above, it will be readily understood by those skilled in this art that the respective expiratory and inspiratory limbs 18 and 16, and inlet and outlet conduit portions 128 and 130 could be integrally made and/or permanently joined together, and detachable connections as indicated by lines 132 and 134 utilized for the operable joinder thereof to the inlet and outlet conduits 120 and 122.

By the above description is believed made clear that a substantially closed fluid flow circuit is provided to extend from the trachea of the patient 12, through the endotracheal tube 70, expiratory passage 22, inlet conduit portion passage 137, inlet conduit 120, space 121, the barium hydroxide lime charge 110, space 123, outlet conduit 122, outlet conduit portion passage 139, inspiratory 24 and endotracheal tube 70 back to the trachea of the patient 12; with conduit 114 being effective to place pop-off valve 119, the rebreathing bag 118 and/or the non-illustrated ventilator in fluid flow communication with said flow passage, and supply conduits 138 and 140 being effective to supply fresh gas (anesthetic and oxygen) thereto from the anesthetic machine.

The significant advantages provided by the absorber of our invention include the following:

(a) The passage of the expired gases through the warm and moist lime 110, and the heated and highly humid, or saturated, space 123 at the bottom of the absorber will, of course, heat and humidify the gases; while the subsequent passage thereof through outlet conduit 122 which is surrounded by the lime 110 and heated by the exothermic reaction thereof to, for example, 114° F., will function to retain this humidity in the vapor state to prevent the "raining out" thereof, and quite possibly even re-vaporize some of the water carried thereby in the liquid state from the space 123, to insure that the gases exiting from the absorber through outlet conduit 122 will be particuarly warm and humid as set forth in greater detail hereinbelow. Thus may be understood that the absorber of our invention will function to combine the biological heating and humidification of the expired gases by the patient with the chemical heating and humidification of those gases by the exothermic lime-carbon dioxide reaction, to provide particularly warm and humid gases to the inspiratory passage 24 for inspiration by the patient, all to particularly significant biomedical advantage as discussed in some detail hereinabove with regard to the breathing circuit of FIG. 1.

(b) The arrangement of inlet conduit portion 128 to surround the oulet conduit portion 130 will enable the commencement of the heating by the expired gases of the inspired gases almost immediately upon the exit of the latter from the absorber to thus inhibit "raining out" of the humidity in the inspired gases during the transition thereof from the absorber to the inspiratory passage 24 of the single limb circuit.

(c) The provision of fresh gas supply conduits to each of the absorber inlet and outlet conduits 120 and 122, and of proportioning valve 142 to enable the precise proportioning of the anesthetic and oxygen delivered thereto from the anesthetic machine, in turn enables precise control in the humidity of the inspired gases within a readily predictable range; it being understood by those skilled in this art that the relatively cool and dry nature of the fresh gases, and the attendant action thereof in decreasing inspired gas humidity, will, of course, be decreased in proportion to the amount thereof which is introduced into inlet conduit 120 and thus forced to pass through the relatively warm and/or humid environment of the lime 110, space 123, and outlet conduit 122.

(d) The forced passage of the expired gases through the reacting lime charge will insure the sterilization thereof to thus prevent contamination of the ventilator and/or rebreathing bag 118.

(e) The absorber is of relatively compact and straightforward construction in that the absorber inlet and outlet conduits are substantially contained therein and the dome valves are eliminated and replaced with simple, less expensive check valves. Thus, the cost and space requirements of the absorber should be relatively low.

(f) The relative simplicity and low cost of the absorber should make possible the economically feasible production thereof as a disposable item from any suitable, readily available material in the nature of a plastic.

(g) The relative simplicity of the absorber will, if combined with the manufacture thereof from a suitably transparent plastic, make possible the ready and convenient, periodic observation of the essential functions of the absorber by the anesthesiologist so that malfunctions, if any, can be readily detected and remedied.

(h) Since the absorber only requires one fresh gas inflow, namely main supply line 154 to proportioning valve 142, it will be clear that the absorber will be readily utilizable, despite its unique feature of fresh gas inflow proportioning, with the vast majority of existing anesthetic supply machines without modification of the latter.

Figure 4:
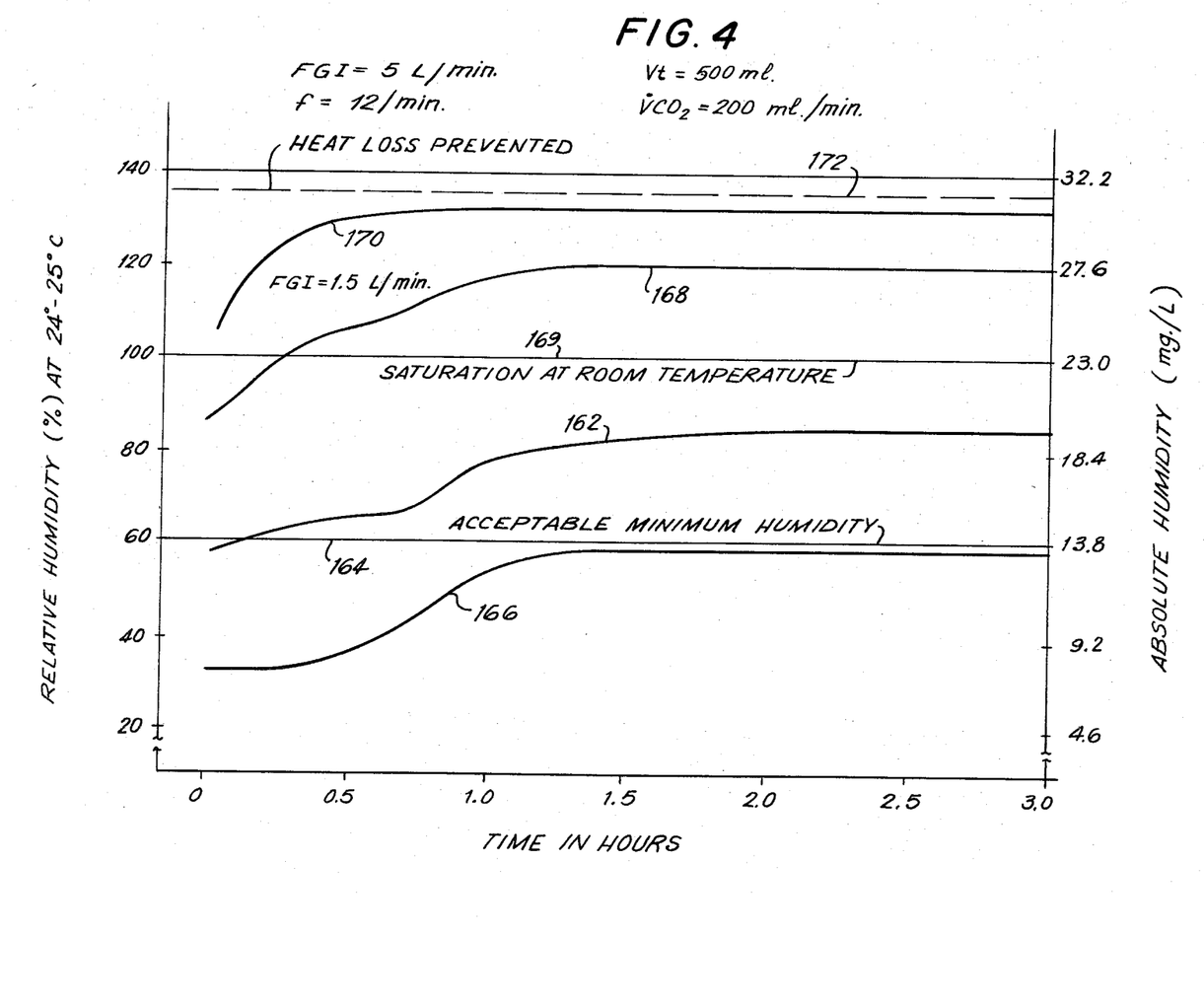
FIG. 4 is a graph illustrating the advantages of the absorber-breathing circuit combination of the invention when compared with those of the prior art.

In very carefully monitored, simulated test use of the novel circuit and absorber combination as depicted in FIG. 2, and referring now to the graph of FIG. 4, it will be readily noted that, with the anesthetic machine set to provide approximately 5 liters/min. of fresh gas inflow (FGI) through valve 142 to outlet conduit 122 and thus inspiratory passage 24, the patient breathing at a rate (f) of approximately 12 times per minute and displacing a tidal volume ($V_t$) of approximately 500 liters per breath, and expelling carbon dioxide at a volume ($VCO_2$) of approximately 200 ml/min., curve 162 of FIG. 4 makes clear that, almost from the beginning of the operation, the relative humidity and absolute humidity of the inspired gases in the near vicinity of the patient end of the breathing circuit will have risen above the respective minimum acceptable levels of 60% and 13.8 mg/L as indicated by curve 164. This may readily be contrasted within the confines of FIG. 4 to the clearly unacceptable relative and absolute humidity levels of approximately 26% and 6.8 mg/L which would be provided as indicated by curve 166 at that exact same point in time during the operation by a conventional absorber of the prior art utilized in conjunction with a conventional, two limbed breathing circuit. Further, after the passage of the first hour of the operation, curve 162 makes clear that the relative and absolute humidity of the inspired gases provided by the absorber-breathing circuit combination of FIG. 2 will have risen to approximately the particularly desirable levels of 80% and 19.8 mg/L, respectively; while the relative and absolute humidity provided by the prior art absorber-double limited breathing circuit combination will remain clearly below the acceptable minimum levels thereof, and will continue to remain therebelow for at least the first approximately 2.8 hours of the operation.

Curve 168 of FIG. 4 depicts the performance of the absorber-circuit combination of FIG. 2 with proportioning valve 142 adjusted to the position thereof of FIG. 2A wherein all of the relatively cool, and dry, fresh gas inflow from the anesthetic machine will be delivered to inlet conduit 120 for passage through the lime 110, the space 123, and the portion of outlet conduit 122 surrounded by the lime, before delivery to the inspiratory passage 24. Under these conditions, curve 168 is believed to make clear that even higher levels of relative and absolute humidity will be provided in the inspired gases, and that those levels will soon exceed the saturation levels of the gases at room temperature as indicated by curve 169.

With proportioning valve 142 precisely calibrated as discussed in some detail hereinabove, it will immediately become clear to those skilled in this art that precise adjustment thereof by a skilled anesthesiologist during the course of an operation will be effective to enable control of the relative and absolute humidity of the gases delivered to the patient through inspiratory passage 24 within the range between curves 168 and 162.

With the fresh gas inflow (FGI) commenced at 1.5 liters/min., or reduced to that level during the course of the operation at the discretion of the anesthesiologist, and all of that inflow being delivered to absorber inlet conduit 120, curve 170 of FIG. 1 makes clear that the relative and absolute humidity levels of the inspired gases in the near vicinity of the patient end of the breathing circuit will be approximately 130% and 30 mg/L, respectively, to thus very closely approach the 135% and 30.9 mg/L relative and absolute humidity levels as indicated by dashed curve 172 and at which any heat loss by the patient due to the cooling and drying effect of the fresh gas inflow is substantially prevented.

Patient rebreathing of carbon dioxide should be inhibited by the absorber-breathing circuit of FIG. 2 to the same advantageous extent as discussed hereinabove with regard to the absorber-breathing circuit combination of FIG. 1.

Figure 3:
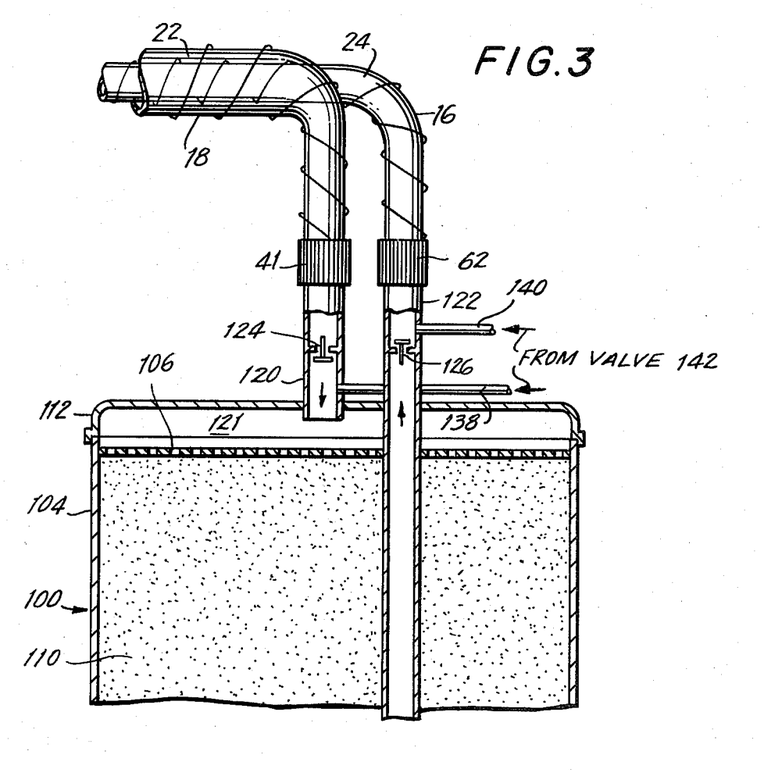
FIG. 3 is a fragmentary, side elevational view of another embodiment of the absorber of FIG. 2 in operable combination with the breathing circuit of FIG. 1 and again includes parts cut away and parts in cross section.

Referring now to the embodiment of the absorber of our invention as depicted at 160 in FIG. 3, that embodiment will readily be seen to be the same as the embodiment of FIG. 2 with the exception that, in the former, each of the absorber inlet conduit 120 and the absorber outlet conduit 122 are terminated above the cannister 104 with resultant elimination of the inlet and outlet conduit portions 128 and 130 of the embodiment of FIG. 2. As a result, the single limb breathing circuit 14 of FIG. 1 may be operatively connected directly to the absorber 160 in the illustrated manner through appropriate use of quick disconnect fittings 41 and 62. A disadvantage of the absorber embodiment 160 as compared to the embodiment 100 of FIG. 2 resides in the fact that some cooling, and attendant "raining out" of the humidity in the humid gases emerging from absorber outlet conduit 122 will occur due to the exposure of the portion of the inspiratory breathing limb 16 which is not surrounded by expiratory breathing limb 18 to the ambient operating room temperature, while a relative advantage thereof might reside in the fact that the same is readily utilizable with many of the double limbed breathing circuits of the prior art in the absence of modification to the latter.

Figure 5:
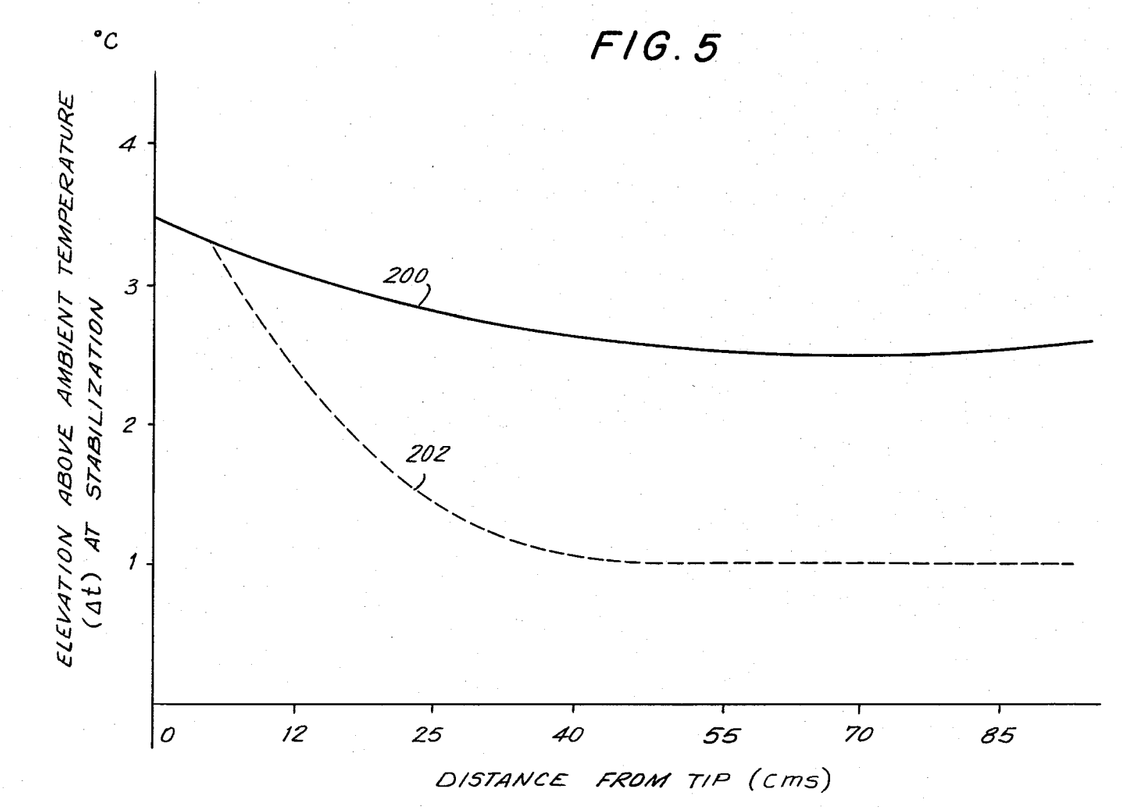
FIG. 5 is a graph illustrating the advantages of the absorber-breathing circuit combination of the invention when compared with said breathing circuit in inventive combination with a prior art absorber.

The significant advantages regarding the increased temperature of the inspired gases, and thus the ability thereof to hold moisture, provided by the new and improved combination of the breathing circuit and absorber of our invention, as compared to the new and improved combination of the breathing circuit of our invention and a prior art absorber, are believed clearly illustrated by the graph of FIG. 5. In that figure, curve 200 represents the inspired gas temperature in the inspiratory tube 24 at the indicated distances from the tip for the former combination, while curve 202 represents those temperatures for the latter; and curves 200 and 202 make clear that, at a distance of approximately 70 centimeters from the breathing circuit tip, a significant temperature increase of approximately 2.5° C., in the inspired gases is provided by the former combination.

Various changes may, of course, be made in the disclosed embodiments of our invention without departing from the spirit and scope thereof as defined in the appended claims.

What is claimed is:

1. A circle absorber anesthetic system for operation in conjunction with an anesthetic machine to anesthetize a patient comprising, in combination:

an absorber including a cannister having an inlet end and an outlet end, means for holding a charge of exothermic water generating reacting carbon dioxide absorbent in said cannister in spaced relation with said two cannister ends whereby to define an open space at each cannister end, an inlet conduit for conveying gases exhaled by a patient extending from outside said cannister into said open space at said inlet end, an outlet conduit for conveying gases from said cannister to said patient for inhalation by said patient and extending from said open space at said outlet end through said cannister including said inlet end to outside of said cannister, said inlet and outlet conduits being disposed in said cannister for conveying exhaled gases flowing into said cannister through said inlet conduit through said carbon dioxide absorbent to the open space at the outlet end of said cannister, and therefrom through said outlet conduit to without said absorber whereby said exhaled gases are stripped in an exothermic water generating reaction with said absorbent, one way valve means in said inlet conduit permitting fluid flow therethrough only into said cannister, and one way valve means in said outlet conduit external of said cannister in heat transfer relationship with the ambient atmosphere for permitting fluid flow therethrough only out of said cannister; and a breathing circuit assembly including a valveless inspiratory breathing tube through which the patient can inhale, a valveless expiratory tube through which the patient can exhale, said inspiratory breathing tube being connectable to said anesthetic machine and the absorber outlet conduit, said expiratory tube being connected to the inlet conduit of said absorber for absorption of exhaled carbon dioxide and reduction of anesthetic pollution of the ambient air, said inspiratory breathing tube being disposed within said expiratory tube and surrounded thereby throughout at least the respective portions of the longitudinal extents of said limbs adjacent the patient for facilitating heat retention of inhaled gases in said surrounded inspiratory breathing tube, said inspiratory and expiratory breathing tubes each comprising an end remote from said absorber, means connected to said remote ends of said inspiratory and expiratory breathing tubes for placing said tube ends in fluid flow communication with a breathing passage of the patient, said inspiratory breathing tube remote end being disposed in close proximity to the said expiratory tube remote end to minimize dead space between said limb ends in which the exhaled gases can collect for direct rebreathing by the patient, whereby the gases exhaled by the patient into said expiratory tube will surround and heat the gases being inhaled by the patient through said inspiratory breathing tube to enable said inhaled gases to hold additional moisture and thereby reduce both the drying effects of said inhaled gases on the breathing passages of the patient and the cooling effects thereof on the patient, and whereby inhalation by the patient through said expiratory tube and exhalation by the patient into said inspiratory breathing tube will be substantially prevented to substantially prevent the rebreathing by the patient of exhaled carbon dioxide through said inspiratory breathing tube, said outlet conduit comprising means for directly and readily picking up heat from said reaction for warming said stripped gases conveyed to said inspiratory breathing tube connected to said outlet conduit open end, said warmed stripped gases being capable of holding a large amount of water vapor for return to said patient through said connected inspiratory breathing tube, whereby said exhaled gases passing through said absorber and exiting said outlet conduit for return to said patient are warmed and humidified; said one way valve means in said outlet conduit being disposed therein for enabling sufficient cooling of said warmed humidified stripped gases to permit formation of a water reservoir in said outlet conduit for maintaining a relatively constant absolute humidity for said gases to be conveyed to said connected inspiratory breathing tube; whereby both heat and moisture loss in said inhaled gases passing through said absorber for conveyance to said patient are minimized.

2. An anesthetic system as in claim 1 further comprising, means to introduce fresh gases from an anesthetic machine into the exhaled gases flowing in said inlet conduit.

3. An anesthetic system as in claim 1 further comprising, means to introduce fresh gases from an anesthetic machine into the gases flowing in said outlet conduit which are to be inhaled by the patient.

4. An anesthetic system as in claim 3 further comprising, means to introduce fresh gases frm an anesthetic machine into the exhaled gases flowing in said inlet conduit.

5. An anesthetic system as in claim 4 further comprising, proportioning valve means for controlling the flow of said fresh gases into said inlet and outlet conduits whereby, the proportion between the amount of said fresh gases which are introduced into said inlet conduit and the amount of fresh gases which are introduced into said outlet conduit may be controlled.

6. A circle absorber anesthetic system for operation in conjunction with an anesthetic machine to anesthetize a patient comprising in combination:

an absorber including a cannister having an inlet end and an outlet end, means for holding a charge of exothermic water generating reacting carbon dioxide absorbent in said cannister in spaced relation with said two cannister ends whereby to define an open space at each cannister end, an inlet conduit for conveying gases exhaled by a patient extending from outside said cannister into said open space at said inlet end, an outlet conduit for conveying gases from said cannister to said patient for inhalation by said patient and extending from said open space at said outlet end through said cannister including said inlet end to outside of said cannister, said inlet and outlet conduits being disposed in said cannister for conveying exhaled gases flowing into said cannister through said inlet conduit through said carbon dioxide absorbent to the open space at the outlet end of said cannister, and therefrom through said outlet conduit to without said absorber whereby said exhaled gases are stripped in an exothermic water generating reaction with said absorbent, one way valve means for permitting fluid flow into said cannister only through said inlet conduit and for permitting fluid flow of said cannister only through said outlet cannister; and a breathing circuit assembly including a valveless inspiratory breathing tube through which the patient can inhale, a valveless expiratory tube through which the patient can exhale, said inspiratory breathing tube being connectable to said anesthetic machine and the absorber outlet conduit, said expiratory tube being connected to the inlet conduit of said absorber for absorption of exhaled carbon dioxide and reduction of anesthetic pollution of the ambient air, said inspiratory breathing tube being disposed within said expiratory tube and surrounded thereby throughout at least the respective portions of the longitudinal extents of said limbs adjacent the patient for facilitating heat retention of inhaled gases in said surrounded inspiratory breathing tube, said inspiratory and expiratory breathing tubes each comprising an end remote from said absorber, means connected to said remote ends of said inspiratory and expiratory breathing tubes for placing said remote tube ends in fluid flow communication with a breathing passage of the patient, said inspiratory breathing tube remote end being disposed in close proximity to the said expiratory tube remote end to minimize dead space between said limb ends in which the exhaled gases can collect for direct rebreathing by the patient, whereby the gases exhaled by the patient into said expiratory tube will surround and heat the gases being inhaled by the patient through said inspiratory breathing tube to enable said inhaled gases to hold additional moisture and thereby reduce both the drying effects of said inhaled gases on the breathing passages of the patient and the cooling effects thereof on the patient, and whereby inhalation by the patient through said expiratory tube and exhalation by the patient into said inspiratory breathing tube will be substantially prevented to substantially prevent the rebreathing by the patient of exhaled carbon dioxide through said inspiratory breathing tube, said outlet conduit comprising means for directly and readily picking up heat from said reaction for warming said stripped gases conveyed to said inspiratory breathing tube connected to said outlet conduit open end, said warmed stripped gases being capable of holding a large amount of water vapor for return to said patient through said connected inspiratory breathing tube, whereby said exhaled gases passing through said absorber and exiting said outlet conduit for return to said patient are warmed and humidified; said one way valve means in said outlet conduit being disposed therein for enabling sufficient cooling of said warmed humidified stripped gases to permit formation of a water reservoir in said outlet conduit for maintaining a relatively constant absolute humidity for said gases to be conveyed to said connected inspiratory breathing tube; whereby both heat and moisture loss in said inhaled gases passing through said absorber for conveyance to said patient are minimized.

7. A circle absorber anesthetic system for operation in conjunction with an anesthetic machine to anesthetize a patient comprising in combination:

an absorber including a cannister having an inlet end and an outlet end, means for holding a charge of exothermic water generating reacting carbon dioxide absorbent in said cannister in spaced relation with said two cannister ends whereby to define an open space at each cannister end, an inlet conduit for conveying gases exhaled by a patient extending from outside said cannister into said open space at said inlet end, an outlet conduit for conveying gases from said cannister to said patient for inhalation by said patient and extending from said open space at said outlet end through said cannister including said inlet end to outside of said cannister, said inlet and outlet conduits being disposed in said cannister for conveying exhaled gases flowing into said cannister through said inlet conduit through said carbon dioxide absorbent to the open space at the outlet end of said cannister, and therefrom through said outlet conduit to without said absorber whereby said exhaled gases are stripped in an exothermic water generating reaction with said absorbent, one way valve means in said inlet conduit permitting fluid flow therethrough only into said cannister, and one way valve means in said outlet conduit external of said cannister in thermally efficient heat transfer relationship with the ambient atmosphere for permitting fluid flow therethrough only out of said cannister; and a breathing circuit assembly including a valveless inspiratory breathing tube through which the patient can inhale, a valveless expiratory tube through which the patient can exhale, said inspiratory breathing tube being connectable to said anesthetic machine and the absorber outlet conduit, said expiratory tube being connected to the inlet conduit of said absorber for absorption of exhaled carbon dioxide and reduction of anesthetic pollution of the ambient air, said inspiratory and expiratory breathing tubes each comprising an end remote from said absorber, means connected to said remote ends of said inspiratory and expiratory breathing tubes for placing said tube ends in fluid flow communication with a breathing passage of the patient, said inspiratory breathing tube remote end being disposed in close proximity to the said expiratory tube remote end to minimize dead space between said limb ends in which the exhaled gases can collect for direct rebreathing by the patient, whereby inhalation by the patient through said expiratory tube and exhalation by the patient into said inspiratory breathing tube will be substantially prevented to substantially prevent the rebreathing by the patient of exhaled carbon dioxide through said inspiratory breathing tube, said outlet conduit comprising means for directly and readily picking up heat from said reaction for warming said stripped gases conveyed to said inspiratory breathing tube connected to said outlet conduit open end, said warmed stripped gases being capable of holding a large amount of water vapor for return to said patient through said connected inspiratory breathing tube, whereby said exhaled gases passing through said absorber and exiting said outlet conduit for return to said patient are warmed and humidified; said one way valve means in said outlet conduit being disposed therein for enabling sufficient cooling of said warmed humidified stripped gases to permit formation of a water reservoir in said outlet conduit for maintaining a relatively constant absolute humidity for said gases to be conveyed to said connected inspiratory breathing tube; whereby both heat and moisture loss in said inhaled gases passing through said absorber for conveyance to said patient are minimized.

* * * * *